(12) United States Patent  (10) Patent No.: US 8,117,675 B2
Strange et al.  (45) Date of Patent: Feb. 21, 2012

(54) WATERPROOF PANTY

(76) Inventors: Valerie Strange, Middleburg, FL (US);
Rochelle Woodeshick, Nescopeck, PA (US); June Krolikowski, Nescopeck, PA (US); Pearl Briggs, Nescopeck, PA (US)

( * ) Notice: Subject to any disclaimer, the term of this patent is extended or adjusted under 35 U.S.C. 154(b) by 0 days.

(21) Appl. No.: 12/930,005

(22) Filed: Dec. 23, 2010

(65) Prior Publication Data
US 2011/0094017 A1  Apr. 28, 2011

Related U.S. Application Data

(63) Continuation of application No. 11/801,071, filed on May 7, 2007, now abandoned.

(51) Int. Cl.
*A41B 9/02* (2006.01)
*A41F 13/20* (2006.01)
(52) U.S. Cl. .............................. 2/406; 2/400; 604/385.3
(58) Field of Classification Search .............. 2/400–408, 2/238; 604/385.01, 385.24, 385.25, 385.3, 604/385.31, 393, 394, 396
See application file for complete search history.

(56) References Cited

U.S. PATENT DOCUMENTS

| | | | | |
|---|---|---|---|---|
| 4,813,950 A | * | 3/1989 | Branch | 604/396 |
| 4,880,424 A | * | 11/1989 | Rautenberg | 604/396 |
| 5,098,419 A | | 3/1992 | Gold | |
| 5,344,698 A | | 9/1994 | Rock et al. | |
| 5,546,607 A | | 8/1996 | Roberts | |
| 5,562,648 A | | 10/1996 | Peterson | |
| 6,149,637 A | * | 11/2000 | Allen et al. | 604/366 |
| 6,195,800 B1 | | 3/2001 | Gilmer et al. | |
| 6,657,099 B1 | * | 12/2003 | Underhill et al. | 604/361 |
| 6,848,121 B1 | | 2/2005 | Halid | |

* cited by examiner

*Primary Examiner* — Gloria Hale
(74) *Attorney, Agent, or Firm* — Thomas R. Shaffer

(57) ABSTRACT

A pretty, stylish and comfortable waterproof panty that has a unique design technique of rolled over welded seams. The rolled over welded seam will inhibit the leaking of bodily fluids at the leg openings caused by stitching and wicking. The panty has an outer shell and an inner panty layer. The outer shell a continuous cut formed of a soft blend laminated fabric. It is liquid proof, breathable, hypo-allergenic, stain resistant, and elastic. It is cut to form a waist opening and two leg openings. If desired stretchable lace or elastic side portions can be provided. The inner panty lining is a breathable soft blend fabric and includes a front portion, back portion and a crotch portion. The crotch portion is double layered for added dryness. The inner panty layer is cut to the full design of the panty having a waist opening and two leg openings. This over all design provides the user peace of mind and security with a stylish, lightweight, comfortable, waterproof panty.

13 Claims, 5 Drawing Sheets

WATERPROOF PANTY

This application is a Continuation of U.S. patent application Ser. No. 11/801,071, filed May 7, 2007 now abandoned.

BACKGROUND OF THE INVENTION

1. Field of the Invention

The present invention relates to women's panties. More specifically, it relates to a panty having a specially configured outer soft blend waterproof laminate fabric shell and an inner layer formed of a soft blend fabric. As used in this patent application, the phrase "soft blend" is hereby defined as a layer of fabric preferably formed of a cotton blend but including any fabric formed from any one or more of the following materials: cotton, cotton blend, polyester blend, microfiber or lace.

2. Description of the Prior Art

There is a strong need for women to have a stylish and pretty lightweight protective waterproof panty to be worn in conjunction with a tampon or sanitary pad during their menstrual cycle offering protection to outer clothing. Women between the ages of 12 to 65 do not have access to a colorful and stylish protective panty made for their active lifestyles.

Every woman has experienced the fear of unexpected leaks and stains to their outer clothing. Briefs with some limited areas of protection offer one of the few available options. These prior art briefs offer one or more of the following: waterproof sections, water-repellent applications, and extra padding to absorb the liquid. These protective undergarments do not offer the look and comfort of everyday panties. They also do not provide the user with a secure leg that prevents leaking through the stitching and wicking out through the leg opening. Examples of some of the prior art panties which have been proposed include the following.

U.S. Pat. No. 5,546,607 discloses a hygienic panty that has a narrow strip (central segment) of waterproof material. All of the embodiments reflect different arrangements of utilizing padding causing bulkiness. There is also stitching that extends through the entire thickness or at least through the outermost layers and around the leg openings that can cause leaking and wicking to outside clothing.

U.S. Pat. No. 4,880,424 provides a panty which has a laminated crotch portion and the laminated crotch portion is exposed to the skin. This garment has a snug exposed leg elastic, which if not properly tensioned will cause discomfort to the wearer. Further, with this design, wicking will occur at the leg opening.

U.S. Pat. No. 5,098,419 provides a coated liquid resistant crotch portion. This garment is sewn allowing needle holes that may leak. Elastic is also sewn in at the leg openings that may lead to leaking and wicking to the outside of garment.

Because a stylish and pretty protective panty is not available, women often resort to doubling up on their protection such as, wearing a tampon with a sanitary pad in case leaking occurs. Women also resort to wearing two large sanitary pads at one time, making frequent trips to the bathroom to check their panties for leakage to outer clothing, and wearing dark colors to conceal any unexpected stains. Staining can occur when a tampon leaks, when a sanitary napkin shifts or becomes overly full, or when a woman unexpectedly starts her menstrual cycle.

SUMMARY OF THE INVENTION

The present invention has a number of innovative characteristics. First, approximately 75% to 100% (depending on style) of the panty garment of the present invention is protected by a waterproof laminated fabric and by the precise continuous cut of the outer shell. There are no crotch seams, so there is no chance of leaking because of needle holes in the outer shell.

A soft blend fabric is used as an inner panty layer on the inside of the garment. It is cut to the full design of the panty. The soft blend fabric is doubled at the crotch area for added dryness. This fabric allows for moisture vapor transmission, allows sanitary pads with adhesive strips to stick securely. Further it is breathable and it is comfortable against the skin. The soft blend inside portion is "welded" to the laminated fabric with an adhesive so there are no needle holes to leak.

The design of the present invention contemplates that approximately ⅛" of laminate will extend past the soft fabric inside around the leg openings to inhibit wicking. Further, our unique design technique of "rolling over" the laminated side of the fabric to the outside at the leg openings creates a waterproof tube portion for the elastic to run through. Alternatively, an elastic adhesive can be used instead of a strip of elastic material. This will inhibit leaking and wicking of bodily fluids to the outside garment and clothing.

An additional feature of the present invention is that the panty is pretty and has the same basis look and feel of conventional women's panties (which are not waterproof). The present invention provides a pretty, a stylish, discreet and comfortable waterproof panty for women that features a unique design technique of rolled over welded seams. The waterproof panties that are currently available have an undesirable brief design and have some have a diaper-like feel and they do not offer leak-proof and wick resistant leg openings.

Almost every woman has experienced the fear, panic and embarrassment of an unexpected leak during the menstrual cycle. One object of the present invention is to offer both the look and feel of regular panties with the total protection in all areas of the panty from unwanted leaks onto outer clothing when used in conjunction with a sanitary napkin or a tampon.

Previous panty designs have not been able to stop the leaking of fluids through the leg openings. Their leg openings either have needle holes which allow the fluid to leak through or they have no barrier to prevent wicking. Wicking occurs when the fluid makes its way to the leg opening and the fabric or elastic carries it around to the outside of the panty. Another object of our invention is to stop the leaking and wicking onto the outside of the panty which leads to the staining of outer clothing. Our present invention offers a leg opening with a rolled laminated seam that uses no stitching. Since it is welded with an adhesive, there are no needle holes in the laminated fabric to cause leakage or wicking. This rolled leg also serves as a barrier to prevent wicking on to the outside of the panty. The panty of the present invention is waterproof but is not intended to be completely water-tight and to completely prevent all leaking in all possible situations or scenarios. If someone experiences an unusually large gush of fluids or a hemorrhage, the panty may leak due to the capacity of the panty itself. However, if used with a tampon or sanitary pad, normal flow will be contained. The only way known to protect against unusually large amounts of liquid is to provide an adult diaper or other garment that has excessive padding or other absorption material to absorb the liquid. The use of such padding or absorption materials, however, would defeat essential goal and purpose of the present invention, namely, to create a waterproof panty that looks and feels like a regular pair of women's panties.

One part of the present invention is the provision of an outer shell which has a continuous cut of a soft blend laminated fabric. This laminated fabric gives total protection throughout the entire panty. This continuous piece of a laminated fabric with no stitching at the crotch area or leg openings eliminates the possibility of leakage through needle holes. The use of an outer shell which has no seams or needle holes eliminates the leakage of fluids in the front and back part of the panty of the present invention. This allows for a restful night of sleep when the fluid has a tendency to creep up the back or front of a panty and ruin bed sheets.

The laminate is then covered by an inner panty layer formed of a breathable and comfortable soft blend fabric. This soft blend fabric covers the inside of the panty to give it an extremely soft feel. Another object of our invention is to offer the wearer a comfortable fit with a natural based fiber. This fabric also offers a secure surface that easily holds a sticky backing of a sanitary napkin. The laminate itself is durable, flexible, hypoallergenic, liquid-proof, breathable and elastic.

Last but not least, a part of our invention has to do with style and color. Another object or all of our invention is to offer women a choice of color and style. This panty will be made in different styles and colors determined by current trends. This panty will offer the same quality of protection against leakage but will be made to fit different body types. These and further objects of the invention can be moved more fully understood from the following description of the invention.

DETAILED DESCRIPTION OF THE PREFERRED EMBODIMENTS

Figure 3:
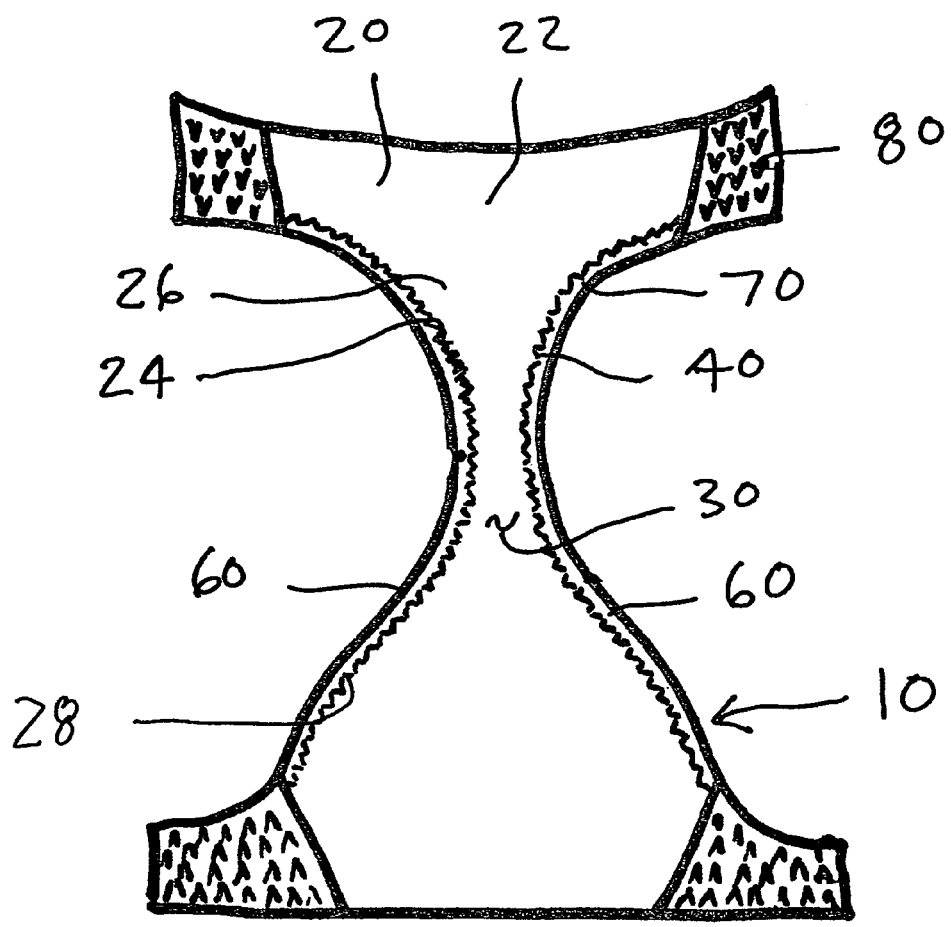
FIG. 3 is top plan view of the outer shell of the present invention.

Referring to the figures, a waterproof panty 10 is shown which includes an outer shell 20 formed of a soft blend waterproof laminate fabric. The outer shell 20 has an outer shell surface layer 22 formed of a soft blend and has a waterproof inner shell layer 28 formed of a breathable waterproof fabric. The outer shell surface layer 22 and said inner shell layer 28 are securely bonded together to form a single outer shell laminate fabric material 20. The outer shell 20 is formed from a single sheet of laminate fabric and has a generally hour glass shape (FIG. 3). The outer shell 20 includes a crotch area 30 and leg edge portions 40. The outer shell 20 has no crotch seams and no needle punctures in the crotch area 30. Preferably, no needle punctures are provided in any portion of the outer shell 20.

Figure 4:
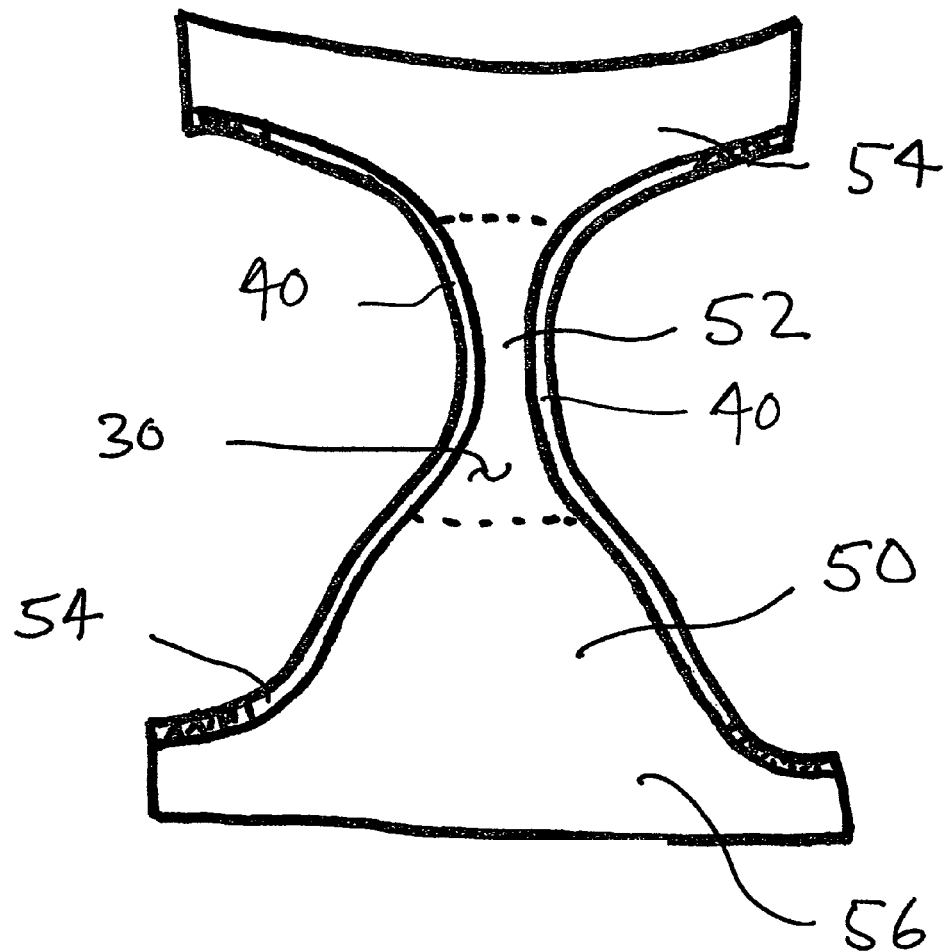
FIG. 4 is a top plan view of the inner panty liner of the present invention.

An inner panty layer 50 is formed of a soft blend fabric. The inner panty layer 50 has substantially the same shape and size as the outer shell 20 as is shown in FIG. 4. The inner panty layer 50 is welded with a polyurethane adhesive to the inner shell layer 28 of the outer shell 20. The said inner panty layer 50 covers substantially all of the surface area of said waterproof inner shell layer 28 (except for an ⅛ inch wide strip around the leg which is described below). This causes the waterproof inner shell layer 28 to be essentially sandwiched between two layers of a soft blend fabric, namely outer shell surface layer 22 and inner panty layer 50. Because a substantial portion of the both the inside 50 and outside 22 of the panty 10 are covered with a soft blend fabric, the panty has the look and feel of a conventional or regular non-waterproof women's panty.

The inner panty layer 50 preferably does not extend all the way to and does not cover the leg edge portions 40 of said outer shell 20. Preferably the leg edge portions 40 include a waterproof tube portion 60 formed by a perimeter edge portion 24 of the outer shell 20 being folded outwardly with a perimeter edge 24 of said outer shell surface layer 28 being welded with a polyurethane adhesive to an interior portion 26 of said outer shell surface layer 22. With this arrangement, the waterproof inner shell layer 28 covers the entire exterior of said waterproof tube portion 60.

An elastic member (or elastic adhesive) 70 (FIG. 5) is provided inside said waterproof tube portion 60 to secure said leg edge portions 40 against the legs of a wearer of the panty 10. The waterproof tube portion 60 prevents the wicking of fluids from said inner panty layer 50 to said outer shell surface layer 22. Preferably, said waterproof inner shell layer 28 extends beyond the tube portion 60 on to the outer shell surface 22 for a distance "d" of approximately ⅛ of an inch.

The inner panty layer 50 is preferably doubled as shown at 52 (FIG. 4) in the crotch area 30 for added dryness. The panty layer 50 allows for moisture vapor transmission. Further, the inner panty layer 50 allows sanitary pads with adhesive strips to stick securely. Still further, the inner panty layer 50 is breathable and comfortable against the skin.

It is preferred that waterproof inner shell layer 28 be formed of a polyurethane film having a thickness of approximately 1 mil or less This waterproof inner shell layer 28 is preferably liquid proof, breathable, elastic, hypo-allergenic and stain resistant.

The panty 10 of the present invention may be formed to one of a variety of panty designs such as bikini, low rise, shorty, thong or brief. Further, the outer shell surface layer 22 of the panty 10 may be dyed to a desired color. Alternatively, the outer shell surface layer 22 may be formed of a material having a colorful fabric design, for example.

Figure 1:
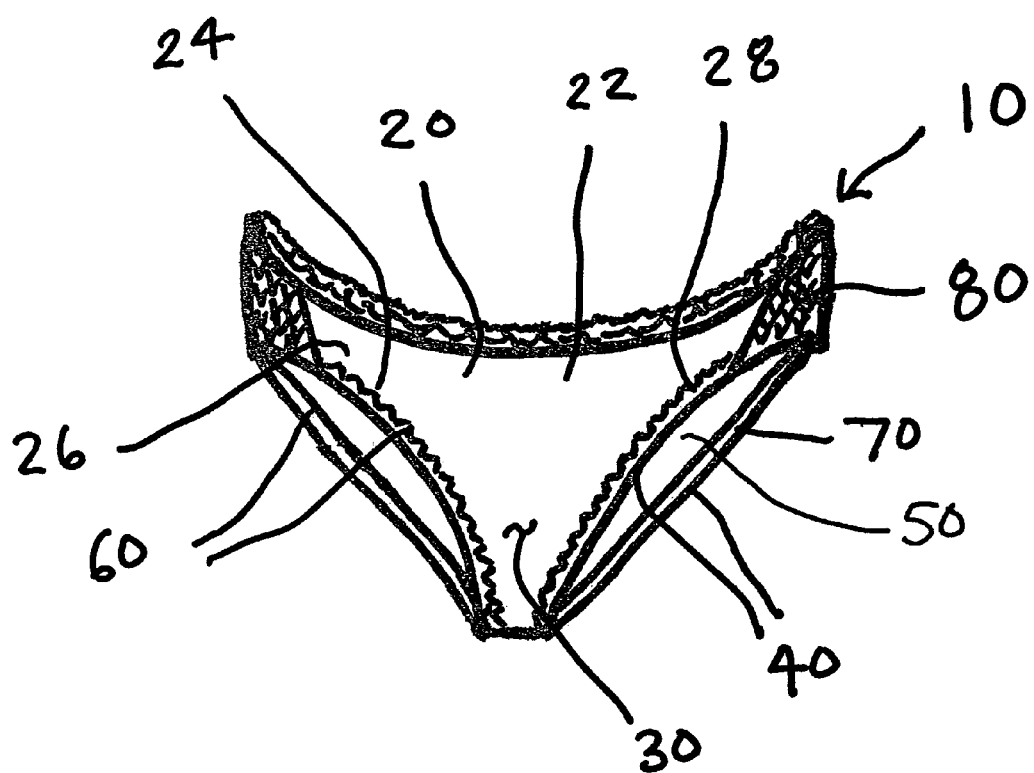
FIG. 1 is a front plan view of the panty of the present invention.
Figure 2:
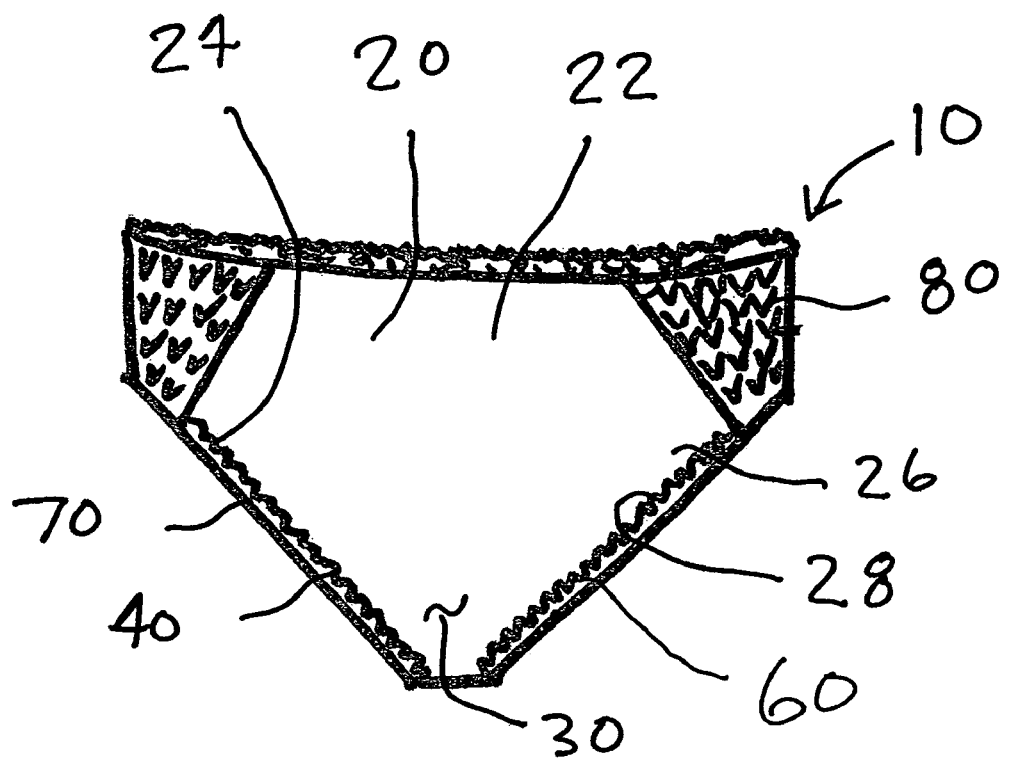
FIG. 2 is a rear plan view of the panty of the present invention.

As best shown in FIGS. 1 and 2, a portion 80 of the panty 10 may be formed of stretch lace with a soft blend backing attached. The panty may alternatively comprise a portion 80 formed of decorative elastic with a soft blend backing attached.

The waterproof panty 10 according to the present invention preferably has between 75% and 100% of its surface area protected with said waterproof inner shell layer 28. The only portions which would not be so protected would be areas covered by stretch lace or decorative elastic 80.

The outside 22 of laminated fabric 20 is a soft blend stretch fabric. The inside of the laminate 20 is a polyurethane film layer 28 that is liquid roof, breathable, elastic, hypo-allergenic and stain resistant. As mentioned, stretch lace or decorative elastic 80 with a soft blend backing attached may be provided. The laminated fabric outer shell 20 is rolled over itself in the leg portions 40 exposing the waterproof layer 28 around the leg opening. End 24 is welded with a polyurethane adhesive to an interior portion 26 of outer shell layer 22 around the leg opening leaving a waterproof tube portion 60 for elastic 70 to be run through or, alternatively, elastic adhesive may be used.

Stretch lace or elastic waist 80 and threads that can be used are regular nylon for added strength, stretch nylon for stretch ability as well as strength and softness, and polyester thread for durability.

The inner panty layer 50 is a soft blend fabric which consists of a front portion 54, back portion 56 and a crotch portion

Figure 5:
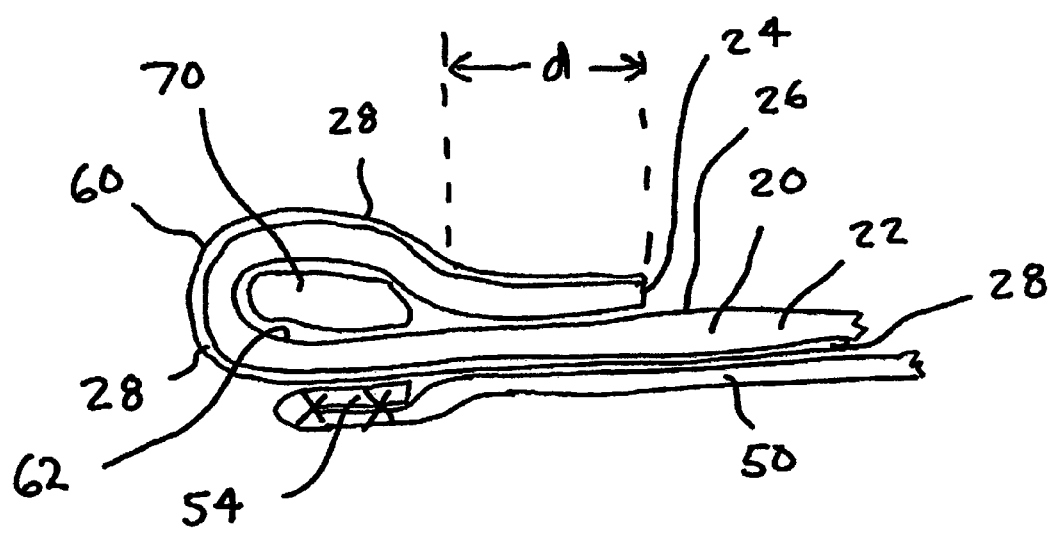
FIG. 5 is a cross sectional view of a leg portion and waterproof tube portion of the present invention.

30. Inner panty layer 50 is cut to the full design of the garment 10. The front 54 and back 56 portions are sewn to the crotch portion 30 joining all three pieces. The crotch portion 30 is a double layer of soft blend fabric 52 for added dryness. The outside edge 54 is folded back and sewn for a finished edge (FIG. 5). This soft blend fabric is used because of its wicking ability and because it has excellent comfort against the skin. The inner panty layer 50 of the garment 10 will preferably be dark colors such as black, brown and dark green, for example. This choice of color will control the appearance of staining in the panty.

The outer shell surface layer 22 of outer shell 20 is a soft blend stretch that is laminated with a polyurethane film that is liquid proof, breathable, elastic, hypo-allergenic and stain resistant. The outer shell 20 is preferably no more than 1.0 ml. in thickness. The outer shell 20 is cut to extend ½" to 1" (depending on the design of panty) past the edge of inner panty layer 50 soft blend lining. The outer shell 20 is then rolled over to the front of the garment 22 leaving a ⅛" of laminate 28 exposed on the inside around the leg openings. This ⅛" strip of waterproof laminate 28 helps to keep bodily fluids from getting to the outside of the garment. The inner panty layer 50 is then welded to the waterproof inner shell layer 28 with a polyurethane adhesive. This provides for a smooth, flat, soft seam, and is another step in providing for a leak-proof leg opening 40.

The outer shell 20 has an outer shell surface layer 22 which is the soft blend side of the laminated fabric 20. The outer shell 20 is cut in accordance with specific design of the panty 10. In FIGS. 1-3, for example, a lace hip bikini, covers approximately 75% of the back and front of the panty. A lace material 80 covers the remaining 25%. The outer shell 20 is a continuous cut from back to front with no seam, especially no crotch seam thus ensuring there will be no leaking through a crotch seam. This is yet another step in providing a truly waterproof panty 10. The cut is precise as to give a smooth, flat comfortable fit.

In this design of panty 10, a stretch lace or elastic 80 is provided over a matching color lining of soft blend fabric. This stretch lace or decorative elastic 80 is used to give more stretch and comfort. Lace 80 is attached to outer shell surface layer 22 at the side/hip area of the front and back of the garment. This is done by sewing or welding with a polyurethane adhesive to ensure a smooth seam.

The laminated fabric layer 20 is "rolled over" to the outside 22 of the panty 10 around the leg opening 40. The edge 24 can be cut in a decorative design or lace or trim may be added to keep the panty pretty. Edge 24 of layer 20 is then welded with a polyurethane adhesive to outer shell surface layer 22 allowing for a ⅛" to ¼" (depending on design of panty) waterproof tube portion 60 which forms a shaft 62 for the leg elastic 70. Leg elastic 70 is adjusted for a secure and comfortable fit, depending on design of panty. Elastic (or elastic adhesive can be used) 70 is then run through the waterproof tube portion 60 and up to the sides of the garment, and sewn to secure at ends. These two steps are the final steps in producing a waterproof garment unlike any other. There is no more worry about leaking through at the leg area 40. Because the "roll over" forming tube portion 60 is the laminated side 28 of fabric 20, it will not wick, and the elastic (or elastic adhesive) 70 is put through the waterproof tube portion and adjusted for design, for a secure and comfortable fit. Side seams are sewn or welded together and a waistband is sewn or welded to the garment. The waistband can be a stretch lace or elastic.

It is to be understood that while certain forms of the present invention have been illustrated and described herein, the present invention is not to be limited to the specific forms or arrangements of parts described and shown and may be otherwise practiced within the scope of the following claims.

We claim:

1. A waterproof panty comprising:
    a) an outer shell formed of a waterproof laminate fabric, said outer shell including an outer shell layer formed of a material formed from any one of cotton, a cotton blend and a polyester blend, said outer shell also including a waterproof inner shell layer formed of a breathable waterproof fabric, wherein said outer shell layer and said inner shell layer are bonded together to form a laminate material, said outer shell, when laid out flat, having a generally hour glass shape including a crotch area and leg edge portions, said outer shell having no crotch seams and no needle punctures in said crotch area; and
    b) an inner panty layer formed of a material formed from any one of cotton, a cotton blend and a polyester blend, said inner panty layer having substantially the same shape and size as the outer shell, said inner panty layer being welded with a polyurethane adhesive to said waterproof breathable inner shell layer whereby said waterproof fabric is sandwiched between said outer shell layer and said inner panty layer.

2. A waterproof panty according to claim 1 wherein said inner panty layer covers substantially all of said waterproof inner shell layer except for a one-eighth inch wide strip around said leg edge portion of said outer shell.

3. A waterproof panty according to claim 1 wherein said leg edge portions include a waterproof tube portion formed by a perimeter edge portion of said outer shell being folded outwardly, said perimeter edge of said outer shell surface layer being welded with a polyurethane adhesive to an exterior portion of said outer shell surface layer, said tube portion having an exterior whereby said waterproof inner shell layer covers the entire exterior of said waterproof tube portion.

4. A waterproof panty according to claim 3 wherein an elastic member is provided inside said waterproof tube portion to secure said leg edge portions against the legs of a wearer of the panty.

5. A waterproof panty according to claim 3 wherein said waterproof tube portion prevents the wicking of fluids from said inner panty layer to said outer shell surface layer.

6. A waterproof panty according to claim 3 wherein said waterproof inner shell layer and the outer shell layer to which the waterproof inner shell layer is bonded extends beyond the tube portion on to the outer shell for a distance of approximately one-eighth of an inch.

7. A waterproof panty according to claim 1 wherein said inner panty layer allows for moisture vapor transmission.

8. A waterproof panty according to claim 1 wherein said inner panty layer is breathable and comfortable against the skin.

9. A waterproof panty according to claim 1 wherein said waterproof inner shell layer is formed of a polyurethane film.

10. A waterproof panty according to claim 1 wherein said waterproof inner shell layer is liquid proof, breathable, elastic, hypo-allergenic and stain resistant.

11. A waterproof panty according to claim 1 wherein said waterproof inner shell layer has a thickness of approximately 1 mil.

12. A waterproof panty according to claim 1 wherein said outer shell layer of said panty is dyed a color.

13. A waterproof panty according to claim 1 wherein said outer shell layer is formed of a material having a colorful fabric design.

* * * * *